US009649088B2

(12) United States Patent
Hirakui et al.

(10) Patent No.: US 9,649,088 B2
(45) Date of Patent: May 16, 2017

(54) ULTRASONIC DIAGNOSTIC SYSTEM AND ULTRASONIC DIAGNOSTIC APPARATUS DOCKING CART (75) Inventors: Katsuya Hirakui, Nasushiobara (JP); Hideo Onodera, Nasushiobara (JP); Takatoshi Okumura, Yaita (JP); Kazuhito Nakata, Otawara (JP); Hironobu Hongou, Otawara (JP); Hiroyuki Shibanuma, Yaita (JP); Takayuki Shiina, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 1592 days.

(21) Appl. No.: 12/552,626

(22) Filed: Sep. 2, 2009

(65) Prior Publication Data
US 2010/0056913 A1    Mar. 4, 2010

(30) Foreign Application Priority Data

Sep. 3, 2008 (JP) .................................. 2008-226180

(51) Int. Cl.
*A61B 8/00* (2006.01)
(52) U.S. Cl.
CPC ............. *A61B 8/00* (2013.01); *A61B 8/4405* (2013.01); *A61B 8/4411* (2013.01); *A61B 8/4427* (2013.01); *A61B 2560/0456* (2013.01)
(58) Field of Classification Search
USPC ....... 600/437; 312/209; 211/4–5; 403/322.1; 710/303
See application file for complete search history.

(56) References Cited

U.S. PATENT DOCUMENTS 5,818,691 A * 10/1998 McMahan et al. ...... 361/679.43
2004/0152982 A1* 8/2004 Hwang et al. ................ 600/441
(Continued)

FOREIGN PATENT DOCUMENTS

CN     1930856 A      3/2007
JP   2001-142566 A    5/2001
(Continued)

OTHER PUBLICATIONS

Office Action issued on Feb. 11, 2011 in the corresponding China Application No. 200910172801.5 (with English Translation).
(Continued)

*Primary Examiner* — Amanda Lauritzen Moher
*Assistant Examiner* — Shahdeep Mohammed
(74) *Attorney, Agent, or Firm* — Oblon, McClelland, Maier & Neustadt, L.L.P.

(57) ABSTRACT

After an ultrasonic diagnosis apparatus is temporally placed on the receptacle of a docking cart to relieve a weight load, the portable ultrasonic diagnosis apparatus is placed at a predetermined position by sliding the apparatus while guiding it along the shapes of the edges of the receptacle. After the portable ultrasonic diagnosis apparatus is slid on the receptacle and rear foot portions come into contact with the stoppers of the receptacle, the front side of the portable ultrasonic diagnosis apparatus is placed on the receptacle. With this operation, front foot portions are fitted in fitting portions, and the portable ultrasonic diagnosis apparatus is placed at an accurate position on the receptacle. In addition, when an operator places the portable ultrasonic diagnosis apparatus on the receptacle or lifts the portable ultrasonic diagnosis apparatus from the receptacle, the fingers which grasp the apparatus are placed in the recessed portions of the receptacle.

18 Claims, 7 Drawing Sheets (56) References Cited

U.S. PATENT DOCUMENTS

| | | | |
|---|---|---|---|
| 2005/0035253 A1* | 2/2005 | Rixom | 248/284.1 |
| 2007/0223190 A1* | 9/2007 | Griffith | G06F 1/1632 |
| | | | 361/679.41 |
| 2008/0078071 A1* | 4/2008 | Gong | 24/373 |
| 2009/0165247 A1* | 7/2009 | Lu et al. | 16/337 |

FOREIGN PATENT DOCUMENTS

| | | |
|---|---|---|
| JP | 2002-542870 A | 12/2002 |
| JP | 2008-89178 A | 4/2008 |
| JP | 2010-57887 A | 3/2010 |

OTHER PUBLICATIONS

Office Action issued Jan. 22, 2013 in Japanese Patent Application No. 2008-226180 with English language translation.

* cited by examiner

ULTRASONIC DIAGNOSTIC SYSTEM AND ULTRASONIC DIAGNOSTIC APPARATUS DOCKING CART

CROSS-REFERENCE TO RELATED APPLICATIONS

This application is based upon and claims the benefit of priority from prior Japanese Patent Application No. 2008-226180, filed Sep. 3, 2008, the entire contents of which are incorporated herein by reference.

BACKGROUND OF THE INVENTION

1. Field of the Invention

The present invention relates to a docking cart for a portable ultrasonic diagnosis apparatus and an ultrasonic diagnosis system including the ultrasonic diagnosis apparatus docking cart and the portable ultrasonic diagnosis apparatus.

2. Description of the Related Art

In ultrasonic diagnosis, the pulsation of the heart or the movement of a fetus can be displayed in real time by the simple operation of bringing an ultrasonic probe into contact with the surface of the body. In addition, this technique is highly safe, and hence allows repetitive examination. Furthermore, this system is smaller in size than other diagnosis apparatuses such as X-ray, CT, and MRI apparatuses, and ultrasonic diagnosis is free from the influence of radiation exposure unlike diagnosis using X-rays. This technique can therefore be said to be a simple diagnosis technique which facilitates examination to be performed by moving the apparatus to the bed side. Ultrasonic diagnosis apparatuses used in this ultrasonic diagnosis vary in type depending on the functions which they have. Some compact apparatuses which have already been developed are small enough to be carried with one hand, and can be used in obstetric treatment, treatment at home, and the like.

Recently, as a system which allows both use at the bed side and portable use, an ultrasonic diagnosis system which connects, for example, a portable compact (portable) ultrasonic diagnosis apparatus to a docking cart such as a dedicated cart or expansion unit has been developed.

The conventional ultrasonic diagnosis system has the following problems. That is, recently, portable ultrasonic diagnosis apparatuses have a tendency to increase in weight. This is because it is required to mount a large-size LCD, enhance functions, and improve image quality even at the expense of some increases in apparatus size and weight. Increasing the weight will place a heavy burden on the operator when attaching and detaching the ultrasonic diagnosis apparatus on or from the docking cart. This problem becomes more noticeable, in particular, when a powerless person performs this attaching/detaching operation. In addition, depending on the appearance designs of an ultrasonic diagnosis apparatus and docking cart, the receptacle of the docking cart may become smaller than the apparatus. In such a case, a place where the ultrasonic diagnosis apparatus should be mounted becomes a blind spot. This can lead to an injury such as being caught between the apparatus and the receptacle.

BRIEF SUMMARY OF THE INVENTION

The present invention has been made in consideration of the above situation, and has as its object to provide an ultrasonic diagnosis system and ultrasonic diagnosis apparatus docking cart which allow even a powerless person to mount an ultrasonic diagnosis apparatus on the receptacle of the docking cart safely, reliably, and quickly regardless of the appearance designs.

In order to achieve the above object, the present invention is configured as follows.

According to an aspect of the present invention, there is provided that an ultrasonic diagnosis system comprising an ultrasonic diagnosis apparatus which acquires ultrasonic image data and a docking cart including a receptacle for installation of the ultrasonic diagnosis apparatus, the receptacle comprising a guide unit to guide the ultrasonic diagnosis apparatus to a predetermined position on the receptacle, and a fitting unit which is fitted on at least part of the ultrasonic diagnosis apparatus guided to the predetermined position by the guide unit to fix the ultrasonic diagnosis apparatus on the receptacle.

According to another aspect of the present invention, there is provided that the system according to claim 1, wherein the receptacle is formed in such a manner that the front side of the docking cart becomes lower in level than the rear side of the docking cart.

DETAILED DESCRIPTION OF THE INVENTION

An embodiment of the present invention will be described below with reference to the views of the accompanying drawing. Note that the same reference numerals denote constituent elements having almost the same functions and arrangements, and a repetitive description will be made only when required.

An ultrasonic diagnosis system according to this embodiment includes a portable ultrasonic diagnosis apparatus and a docking cart for the portable ultrasonic diagnosis apparatus.

Figure 1:
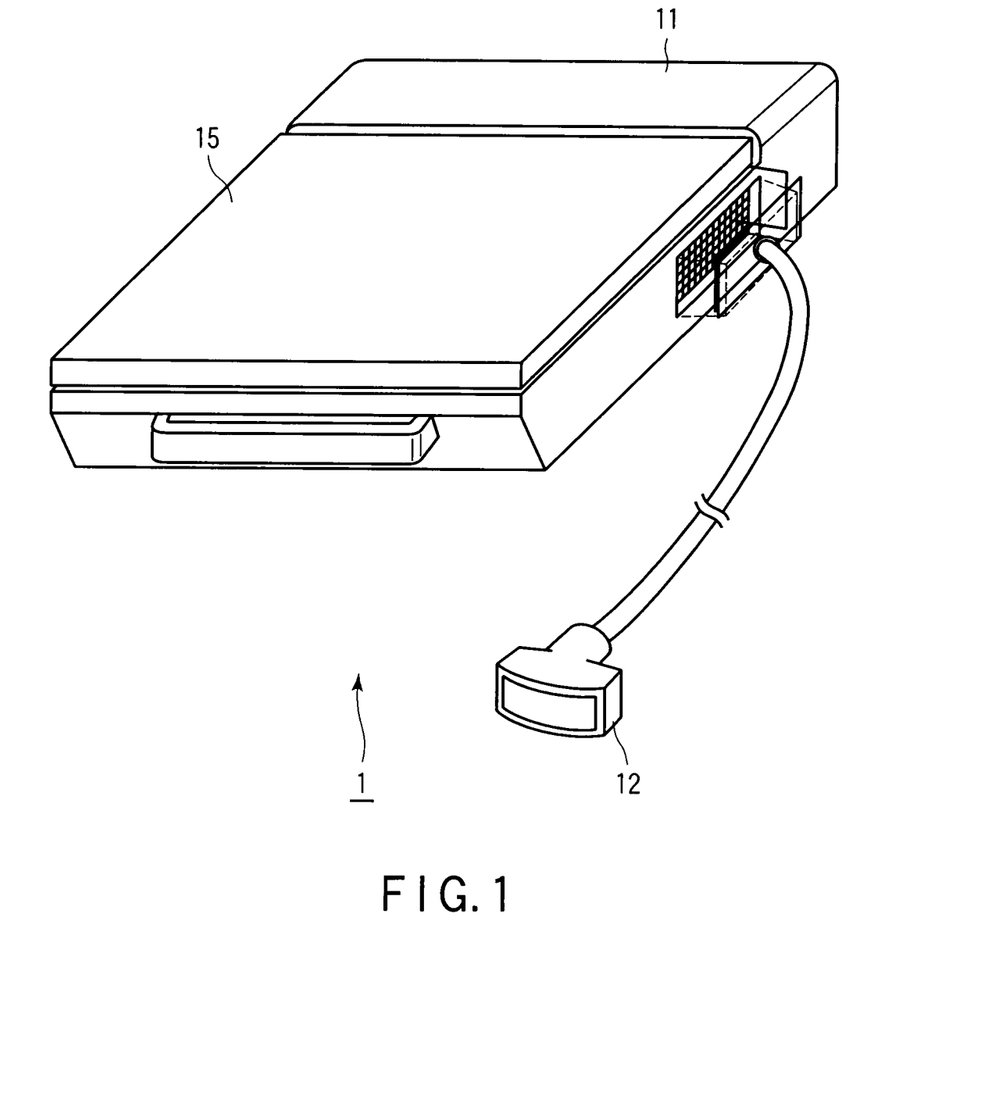
FIG. 1 is a perspective view of a portable ultrasonic diagnosis apparatus 1.
Figure 2:
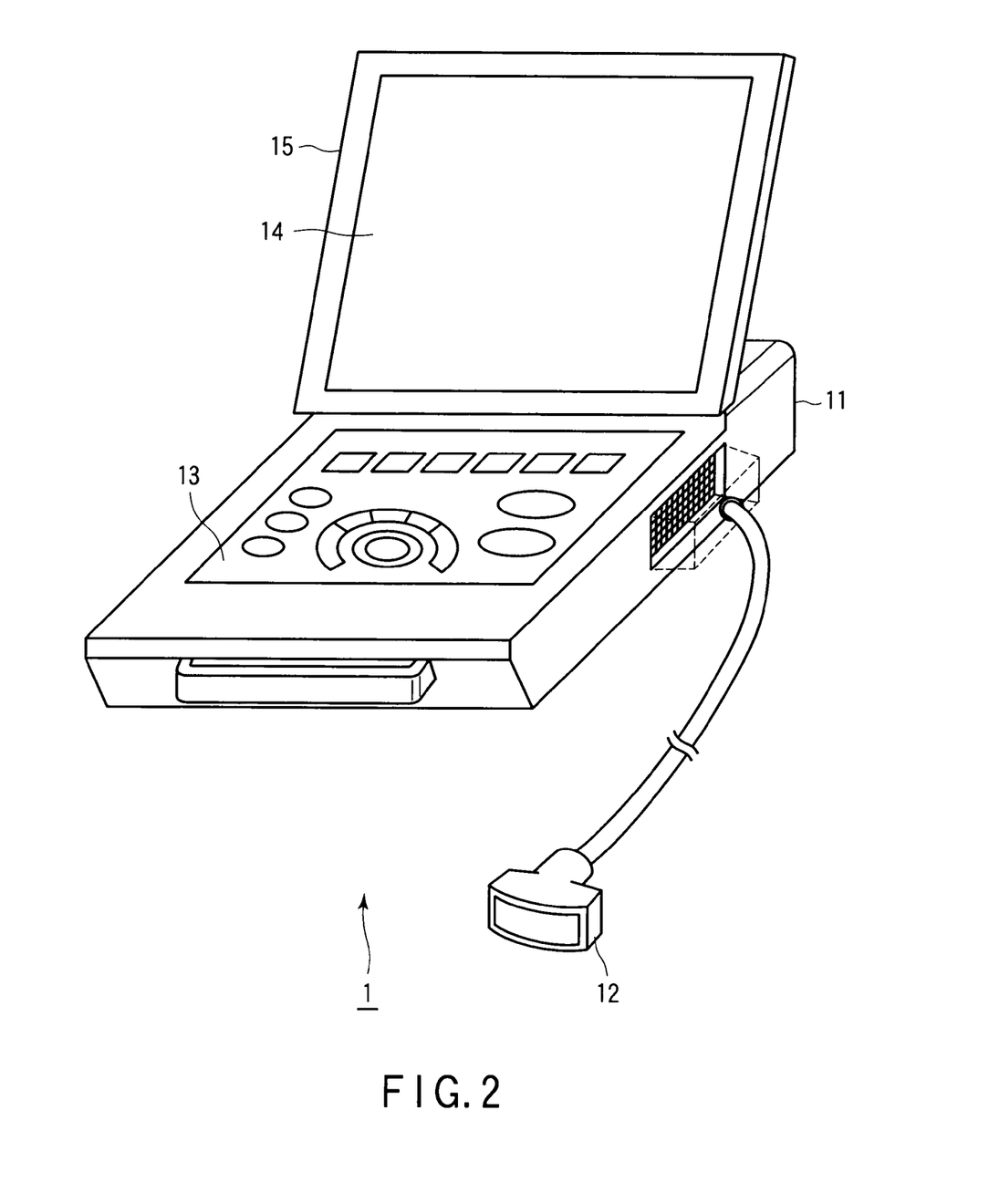
FIG. 2 is a perspective view of the portable ultrasonic diagnosis apparatus 1.

FIGS. 1 and 2 are perspective views of a portable ultrasonic diagnosis apparatus 1. As shown in FIGS. 1 and 2, the portable ultrasonic diagnosis apparatus 1 has, for example, an appearance like a notebook computer or tablet computer, and includes an apparatus body 11, a detachable ultrasonic probe 12, and an openable cover portion 15. Changing the state of the cover portion 15 from the closed state in FIG. 1 to the open state in FIG. 2 can make a monitor 14 and an input device 13 ready for use.

Figure 3:
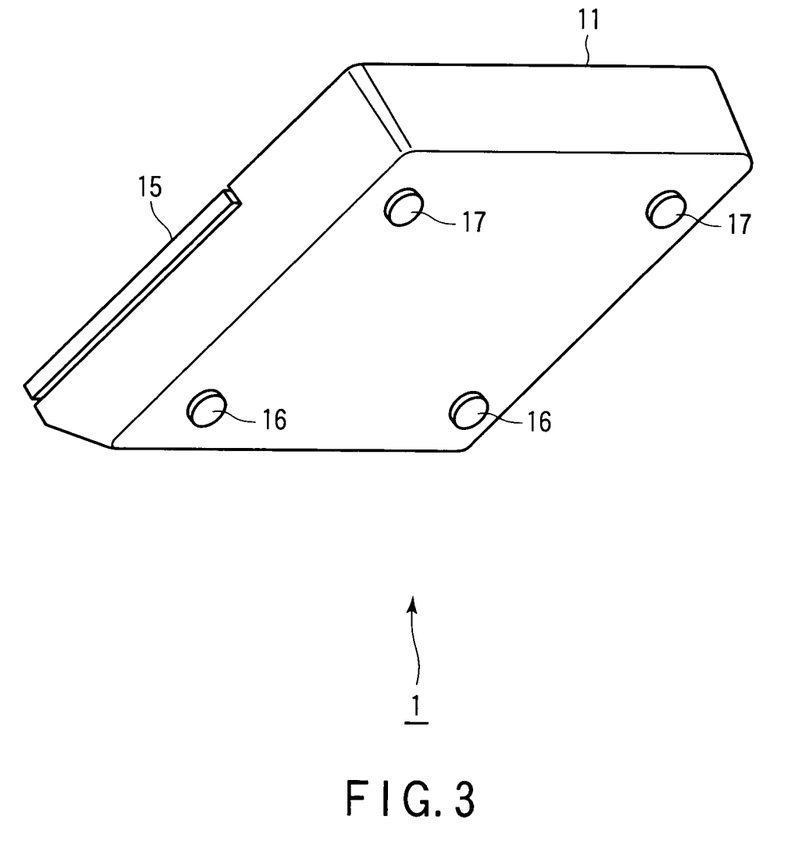
FIG. 3 is a perspective view of the portable ultrasonic diagnosis apparatus 1 viewed from the bottom surface side (i.e., the side which is installed on a docking cart)

FIG. 3 is a perspective view of the portable ultrasonic diagnosis apparatus 1 viewed from the bottom surface side (i.e., the side which is installed on the docking cart). As shown in FIG. 3, the bottom surface of the portable ultrasonic diagnosis apparatus 1 is provided with front foot portions 16 and rear foot portions 17.

Figure 4:
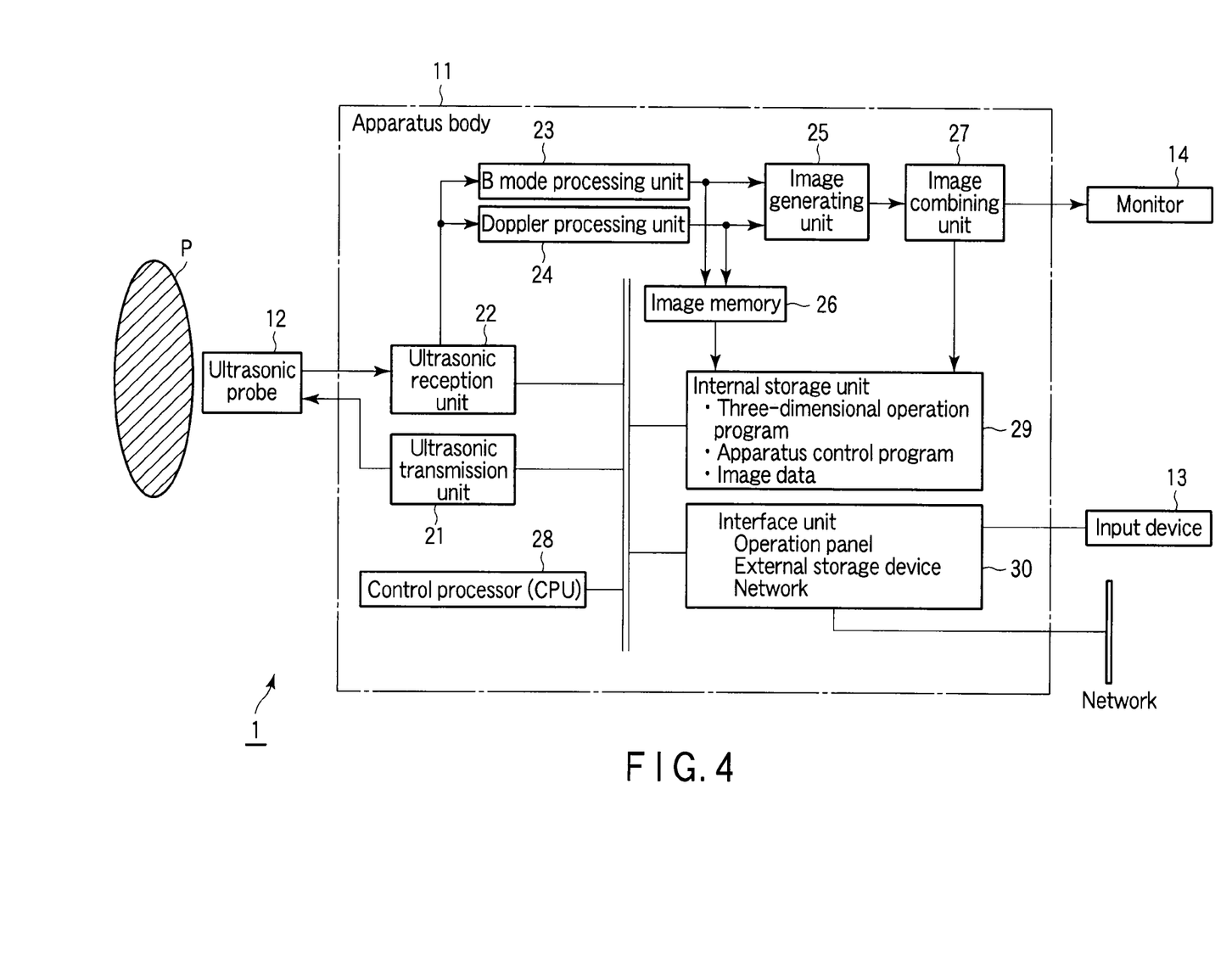
FIG. 4 is a block diagram showing the arrangement of the portable ultrasonic diagnosis apparatus 1.

FIG. 4 is a block diagram showing the arrangement of the portable ultrasonic diagnosis apparatus 1. As shown in FIG. 4, the portable ultrasonic diagnosis apparatus 1 includes the ultrasonic probe 12, the input device 13, the monitor 14, an ultrasonic transmission unit 21, an ultrasonic reception unit 22, a B mode processing unit 23, a Doppler processing unit 24, an image generating unit 25, an image memory 26, an image combining unit 27, a control processor (CPU) 28, an internal storage unit 29, and an interface unit 30.

The ultrasonic probe 12 includes a plurality of piezoelectric transducers which generate ultrasonic waves based on driving signals from the ultrasonic transmission unit 21 and convert reflected waves from an object into electrical signals, a matching layer provided for the piezoelectric transducers, and a backing member which prevents ultrasonic waves from propagating backward from the piezoelectric transducers.

The input device 13 has various types of switches, buttons, a trackball, a mouse, a keyboard, and the like which are used to input, to the apparatus body 11, various types of instructions and conditions, an instruction to set a region of interest (ROI), various types of image quality condition setting instructions, and the like from an operator.

The monitor 14 displays morphological information (B mode images) in the living body, blood flow information (an average velocity image, variance image, power image, and the like), and their combinations as images based on video signals from the image combining unit 27.

The ultrasonic transmission unit 21 includes a trigger generating circuit, delay circuit, and pulser circuit (none are shown). The pulser circuit repeatedly generates rate pulses for the formation of transmission ultrasonic waves at a predetermined rate frequency fr Hz (period: 1/fr sec). The delay circuit gives each rate pulse the delay time required to focus an ultrasonic wave into a beam for each channel and determine a transmission directivity. The trigger generating circuit applies a driving pulse to the probe 12 at the timing based on this rate pulse.

The ultrasonic reception unit 22 includes an amplifier circuit, A/D converter, and adder (none are shown). The amplifier circuit amplifies echo signals received via the ultrasonic probe 12 on a channel basis. The A/D converter gives each amplified echo signal the delay time required to determine a reception directivity. The adder then performs addition processing.

The B mode processing unit 23 receives the echo signal from the ultrasonic transmission unit 21, and performs logarithmic amplification, envelope detection processing, and the like, thereby generating data whose signal strength is represented by a brightness level.

The Doppler processing unit 24 frequency-analyzes velocity information from the echo signal received from the transmission unit 21 to extract a blood flow, tissue, and contrast medium echo component by the Doppler effect, and obtains blood flow information such as an average velocity, variance, and power at multiple points.

The image generating unit 25 generates an ultrasonic diagnosis image as a display image by converting the scanning line signal string for ultrasonic scanning into a scanning line signal string in a general video format typified by a TV format.

The image combining unit 27 combines the image received from the image generating unit 25 with character information of various types of parameters, scale marks, and the like, and outputs the resultant signal as a video signal to the monitor 14.

The control processor 28 has a function as an information processing apparatus (computer) and controls the operation of the main body of the portable ultrasonic diagnosis apparatus.

The internal storage unit 29 stores a data group including control programs for executing a predetermined scan sequence, image generation, and display processing, diagnosis information (a patient ID, findings by a doctor, and the like), a diagnosis protocol, and transmission/reception conditions.

The interface unit 30 is an interface for the input device 13, a network, and a new external storage device (not shown). The interface unit 30 can transfer data such as ultrasonic images, analysis results, and the like obtained by this apparatus to another apparatus via a network.

Figure 5:
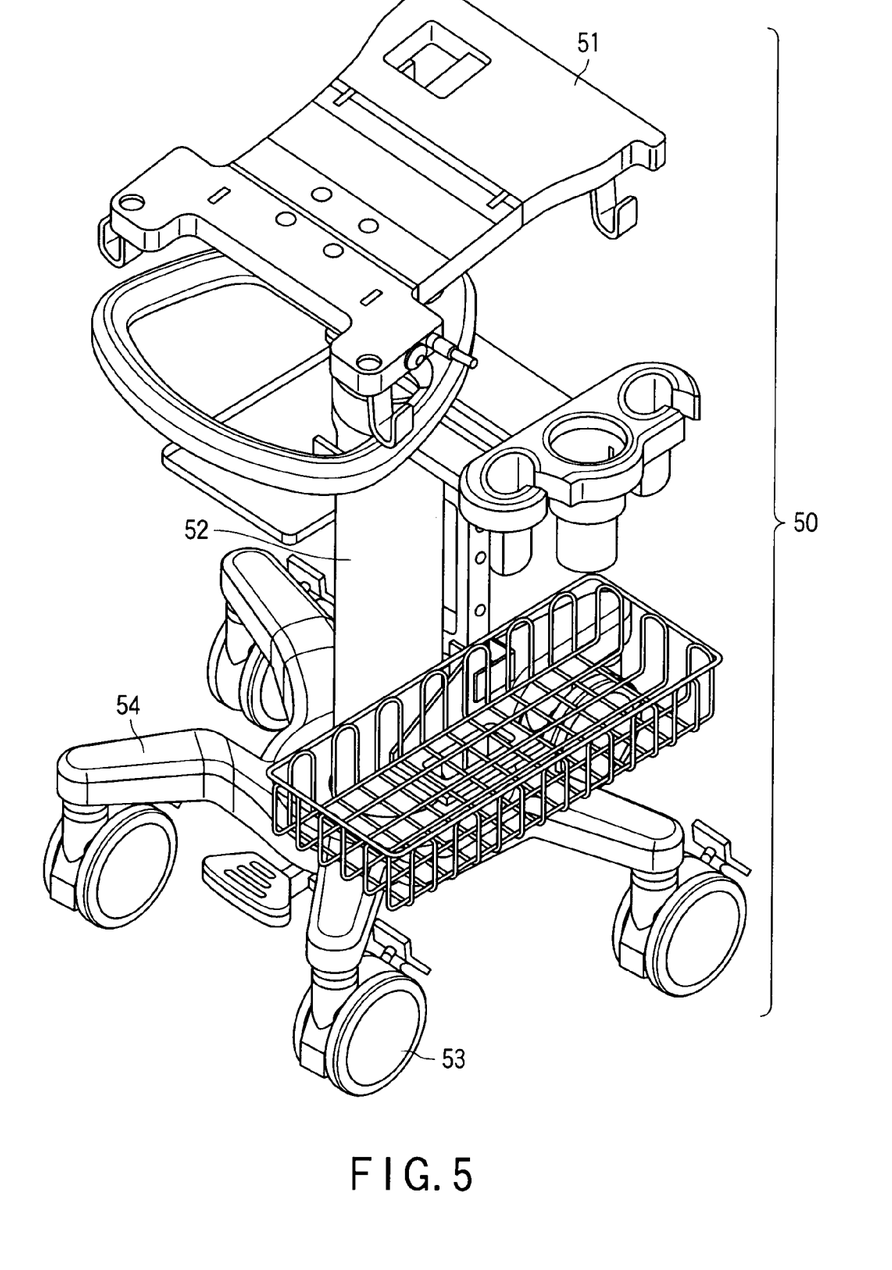
FIG. 5 is a perspective view of a docking cart 50 for the portable ultrasonic diagnosis apparatus 1.

FIG. 5 is a perspective view of a docking cart 50 for the portable ultrasonic diagnosis apparatus 1. As shown in FIG. 5, the docking cart 50 includes a receptacle 51 for installing the portable ultrasonic diagnosis apparatus 1, a column 52 which has an adjusting mechanism for adjusting the level and angle of the receptacle 51 and supports the receptacle 51, wheels 53 to allow the portable ultrasonic diagnosis system to move, and leg portions 54 which are provided with the wheels 53 and support the column 52. Note that when the portable ultrasonic diagnosis apparatus 1 is to be installed or used, the angle of the receptacle 51 is adjusted to make the front side of the portable ultrasonic diagnosis apparatus 1 installed on the receptacle 51 become lower in level than the rear side so as to facilitate the use of the input device 13 and the like.

Figure 6:
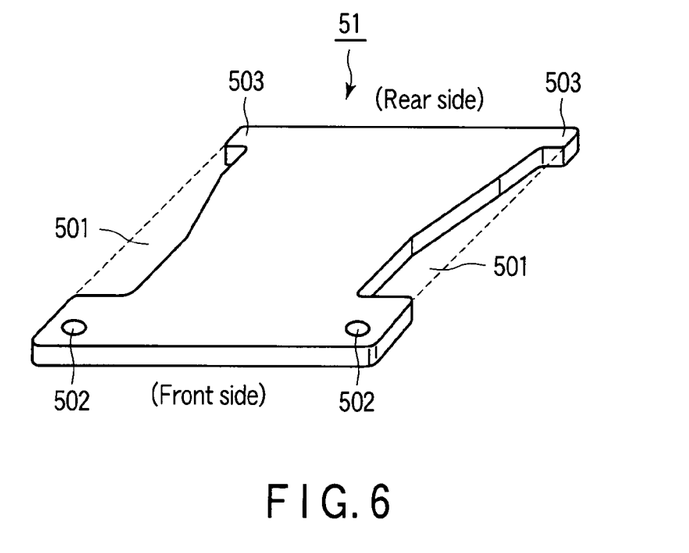
FIG. 6 is a perspective view of a receptacle 51 of the docking cart 50.
Figure 7:
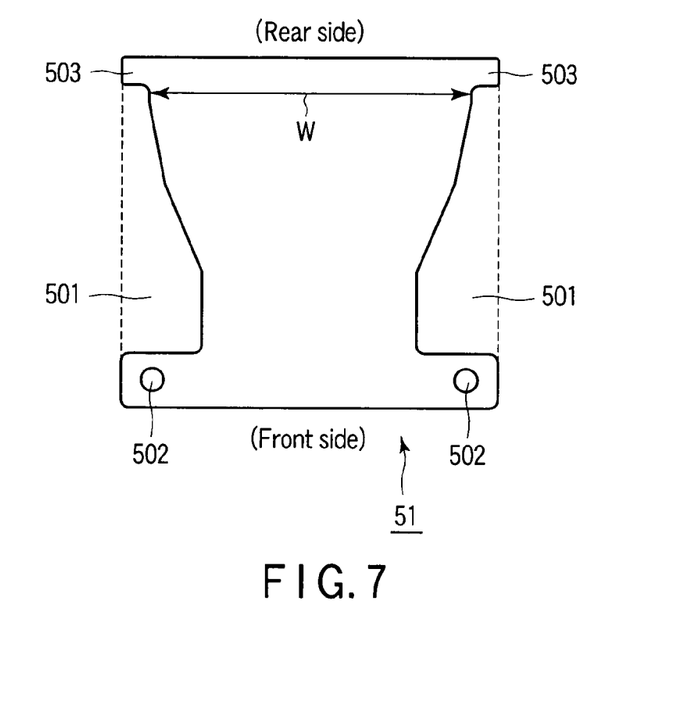
FIG. 7 is a plan view of the receptacle 51.

FIG. 6 is a perspective view of the receptacle 51 of the docking cart 50. FIG. 7 is a plan view of the receptacle 51. As shown in FIGS. 6 and 7, the receptacle 51 has a shape obtained by providing recessed portions 501 for a rectangular plate (the rectangular portion indicated by the dotted lines in FIGS. 6 and 7) corresponding to the size of the bottom surface of the portable ultrasonic diagnosis apparatus 1. Each recessed portion 501 is shaped such that its width increases from the front side of the receptacle 51 to near the middle and gradually decreases toward the rear side. When viewed from the operator side (front side), therefore, the receptacle 51 is constricted from the front side to near the middle and gradually increases in width toward the rear side. In addition, the recessed portions 501 are formed such that a receptacle width W at the rear end positions of the recessed portions 501 becomes equal to the distance between the rear foot portions 17 of the portable ultrasonic diagnosis apparatus 1. The recessed portions 501 are formed to guide the portable ultrasonic diagnosis apparatus 1 to a predetermined position along the shapes of the edges of the receptacle 51 which extend along the sliding direction when the portable ultrasonic diagnosis apparatus 1 is installed on the receptacle 51 while being slid on it.

The receptacle 51 also has fitting portions 502 and stoppers 503. When the portable ultrasonic diagnosis apparatus 1 is to be installed, the fitting portions 502 are fitted on the front foot portions 16 to fix the portable ultrasonic diagnosis apparatus 1 on the receptacle 51. The stoppers 503 are formed at the rear end positions of the recessed portions 501. When, therefore, the portable ultrasonic diagnosis apparatus 1 is to be installed on the receptacle 51 while being slid on it, the rear foot portions 17 come into contact with the stoppers 503 to stop the sliding movement of the portable ultrasonic diagnosis apparatus 1. As a consequence, the portable ultrasonic diagnosis apparatus 1 is placed at a predetermined position.

(Installation/Removal of Portable Ultrasonic Diagnosis Apparatus)

The installation of the portable ultrasonic diagnosis apparatus 1 on the docking cart 50 and the removal of the portable ultrasonic diagnosis apparatus 1 from the docking cart 50 in this ultrasonic diagnosis system will be described next.

Figure 8:
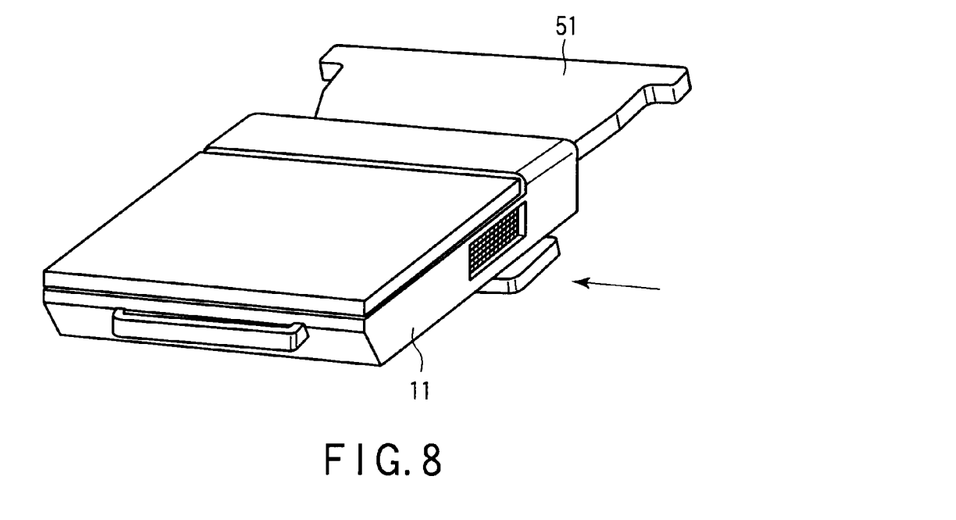
FIG. 8 is a perspective view for explaining a technique of mounting (installing) the portable ultrasonic diagnosis apparatus 1 on the docking cart 50.
Figure 9:
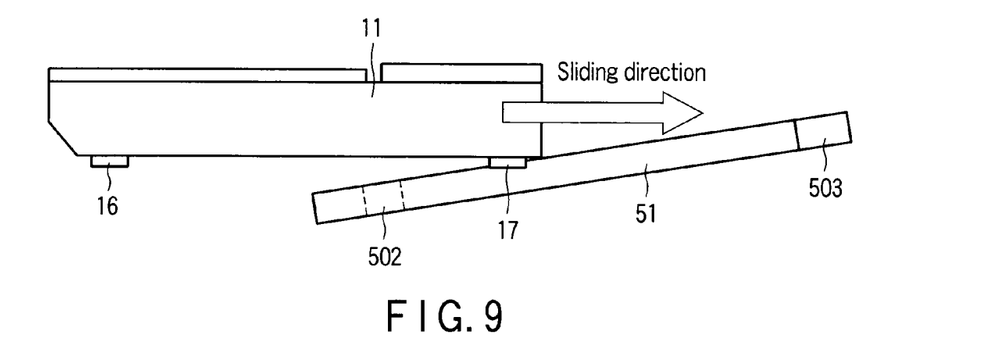
FIG. 9 is a view for explaining the technique of mounting (installing) the portable ultrasonic diagnosis apparatus 1 on the docking cart 50.
Figure 10:
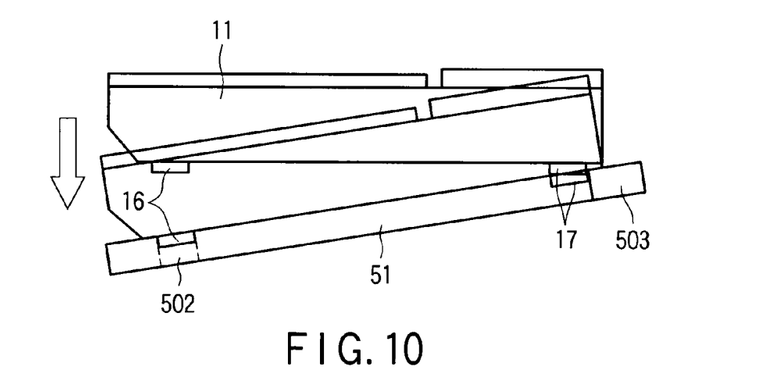
FIG. 10 is a view for explaining the technique of mounting (installing) the portable ultrasonic diagnosis apparatus 1 on the docking cart 50.

FIGS. 8, 9, and 10 are views for explaining a technique of installing (mounting) the portable ultrasonic diagnosis apparatus 1 on the docking cart 50. Note that FIGS. 9 and 10 show the portable ultrasonic diagnosis apparatus 1 and the docking cart, shown in FIG. 8, when viewed from the direction indicated by the arrow. As shown in FIG. 8, part of the portable ultrasonic diagnosis apparatus 1 is placed on the receptacle 51 of the docking cart 50. At this time, one of the front foot portions 16 is placed in one of the recessed portions 501, and the other of the front foot portions 16 is placed in the other of the recessed portions 501 such that the left and right front foot portions 16 are placed across the constricted portion of the receptacle 51.

Note that when the portable ultrasonic diagnosis apparatus 1 is installed on the receptacle 51 such that the left and right front foot portions 16 are placed across the constricted portion of the receptacle 51 in this manner, grasping the two ends of the portable ultrasonic diagnosis apparatus 1 will place the hands or fingers of the person who installs the apparatus at regions between portions of the recessed portions 501 which are located on the front side of the receptacle 51 and portions near the middle (i.e., the widest regions of the recessed portions 501). This can therefore prevent the hands or fingers of the person from being caught between the portable ultrasonic diagnosis apparatus 1 and the receptacle 51 when installing the apparatus 1 on the docking cart 50.

As shown in FIG. 9, then, the operator slides the portable ultrasonic diagnosis apparatus 1 in the sliding direction (from the front side (operator side) of the docking cart 50 to the rear side) while keeping part of the portable ultrasonic diagnosis apparatus 1 in contact with the receptacle 51. With this operation, as shown in FIG. 10, the rear foot portions 17 of the portable ultrasonic diagnosis apparatus 1 move while being guided along the shapes of the edges of the receptacle 51 which extend along the sliding direction. After the rear foot portions 17 of the portable ultrasonic diagnosis apparatus 1 come into contact with the stoppers 503 of the receptacle 51, the front side of the portable ultrasonic diagnosis apparatus 1 is lowered on the receptacle 51. The front foot portions 16 are then fitted in the fitting portions 502. As a consequence, the portable ultrasonic diagnosis apparatus 1 is placed at an accurate position on the receptacle 51.

The operator can remove the portable ultrasonic diagnosis apparatus 1 from the docking cart 50 by grasping the two ends of the portable ultrasonic diagnosis apparatus 1 and pulling it toward him/her while lifting it (i.e., by performing reverse operation to that for installation). At this time, placing the fingers of which grasp the portable ultrasonic diagnosis apparatus 1 in the recessed portions 501 can prevent the fingers of the person who installs from being caught between the receptacle 51 and the portable ultrasonic diagnosis apparatus 1.

(Effects)

According to the above arrangement, the following effects can be obtained.

According to this ultrasonic diagnosis system, after the ultrasonic diagnosis apparatus is temporally placed on the receptacle of the docking cart to relieve the weight load, the portable ultrasonic diagnosis apparatus is placed at a predetermined position by sliding the apparatus while guiding it along the shapes of the edges of the receptacle 51 which extend alone the sliding direction. After the portable ultrasonic diagnosis apparatus is slid on the receptacle and the rear foot portions come into contact with the stoppers, the front side of the portable ultrasonic diagnosis apparatus is placed on the receptacle. With this operation, the front foot portions are fitted in the fitting portions, and the portable ultrasonic diagnosis apparatus is placed at an accurate position on the receptacle. It is, therefore, possible for an operator to minimize the time taken to grasp the portable ultrasonic diagnosis apparatus by himself/herself. It is also possible to place the portable ultrasonic diagnosis apparatus at an accurate position on the receptacle with simple operation. In addition, when the operator places the portable ultrasonic diagnosis apparatus on the receptacle or lifts the portable ultrasonic diagnosis apparatus from the receptacle, the hands or fingers which grasp the portable ultrasonic diagnosis apparatus are placed in the recessed portions of the receptacle. This can prevent the fingers of the person who installs from being caught between the receptacle and the portable ultrasonic diagnosis apparatus. This makes it possible to implement an ultrasonic diagnosis system and ultrasonic diagnosis apparatus docking cart which allow even a powerless person to install an ultrasonic diagnosis apparatus on the receptacle of the docking cart safely, reliably, and quickly regardless of the appearance designs.

Note that the present invention is not limited to the above embodiment, and constituent elements can be variously modified and embodied at the execution stage within the spirit and scope of the invention.

Various inventions can be formed by proper combinations of a plurality of constituent elements disclosed in the above embodiments. For example, several constituent elements may be omitted from all the constituent elements in each embodiment. In addition, constituent elements of the different embodiments may be combined as needed.

As has been described above, the present invention can implement an ultrasonic diagnosis system and the like which allow even a powerless person to install an ultrasonic diagnosis apparatus on the receptacle of a docking cart safely, reliably, and quickly regardless of the appearance designs.

What is claimed is:

1. An ultrasonic diagnostic system comprising:
   an ultrasonic diagnostic apparatus which acquires ultrasonic image data, and includes two foot portions on a bottom surface, the two foot portions placed at predetermined positions separated apart from each other by a predetermined distance; and
   a docking cart including a receptacle for mounting of the ultrasonic diagnosis apparatus,
   the receptacle comprising:
   a main portion positioned at a top of the receptacle and between first and second recessed portions of the receptacle, the main portion configured to guide a sliding of the ultrasonic diagnosis apparatus in a sliding direction by using first and second side surfaces of the main portion, the first and second side surfaces of the main portion limiting a movement of the two foot portions in a width direction perpendicular to the sliding direction by contacting side surfaces of the two foot portions, the first side surface of the main portion opposed to the first recessed portion in the width direction, and the second side surface of the main portion opposed to the second recessed portion in the width direction, and a stopper which stops the sliding of the ultrasonic apparatus at a predetermined position on the receptacle by contacting the side surfaces of the two foot portions, the stopper positioned at a rear side of the main portion in the sliding direction, wherein the main portion has different widths in the width direction, the widths increasing from a front side of the main position to the rear side of the main portion and including a maximum width which is equal to the predetermined distance separating the two foot portions from each other, and wherein the stopper stops the sliding of the ultrasonic diagnosis apparatus when the two foot portions are at a part of the main portion having the maximum width.

2. The system according to claim 1, wherein the first and second recessed portions are formed in the receptacle so as to prevent a hand of a person who grasps and mounts the ultrasonic diagnosis apparatus from coming into contact with the receptacle when at least part of the ultrasonic diagnosis apparatus is mounted on the receptacle.

3. The system according to claim 1, wherein the receptacle is formed such that a front side of the docking cart becomes lower in level than a rear side of the docking cart.

4. The system according to claim 1, wherein the sliding direction is a direction which goes to a rear side of the receptacle from a front side of the receptacle.

5. The system according to claim 1, wherein the main portion is formed along the sliding direction in which the ultrasonic diagnosis apparatus at least partly mounted on the receptacle is slid and moved on the receptacle, and guides the ultrasonic diagnosis apparatus to the predetermined position on the receptacle while being in contact with at least part of the ultrasonic diagnosis apparatus.

6. The system according to claim 5, wherein the first and second recessed portions are formed in the receptacle so as to prevent a hand of a person who grasps and mounts the ultrasonic diagnosis apparatus from coming into contact with the receptacle when at least part of the ultrasonic diagnosis apparatus is mounted on the receptacle.

7. The system according to claim 1, wherein the two foot portions are located on a rear side of the bottom surface in the ultrasonic diagnosis apparatus.

8. The system according to claim 7, wherein the ultrasonic diagnosis apparatus includes two front foot portions other than the two foot portions, the two front foot portions being located on a front side of the bottom surface in the ultrasonic diagnosis apparatus.

9. The system according to claim 8, further comprising a fitting portion including recessed shapes corresponding to shapes of the two front foot portions and that fix the ultrasonic diagnosis apparatus by fitting on the two front foot portions.

10. An ultrasonic diagnostic apparatus docking cart comprising:

a receptacle to mount an ultrasonic diagnostic apparatus which acquires ultrasonic image data and includes two foot portions on a bottom surface, the two foot portions placed at predetermined positions separated apart from each other by a predetermined distance;

a main portion positioned at a top of the receptacle and between a first and second recessed portion of the receptacle, the main portion configured to guide a sliding of the ultrasonic diagnosis apparatus in a sliding direction by using first and second side surfaces of the main portion, the first and second side surfaces of the main portion limiting a movement of the two foot portions in a width direction perpendicular to the sliding direction by contacting side surfaces of the two foot portions, the first side surface of the main portion opposed to the first recessed portion in the width direction, and the second side surface of the main portion opposed to the second recessed portion in the width direction; and a stopper which stops the sliding of the ultrasonic diagnosis apparatus at a predetermined position on the receptacle by contacting the side surfaces of the two foot portions, the stopper positioned at a rear side of the main portion in the sliding direction, wherein the main portion has different widths in the width direction, the widths increasing from a front side of the main position to the rear side of the main portion and including a maximum width which is equal to the predetermined distance separating the two foot portions from each other, and wherein the stopper stops the sliding of the ultrasonic diagnosis apparatus when the two foot portions are at a part of the main portion having the maximum width.

11. The docking cart according to claim 10, wherein the main portion is formed along the sliding direction in which the ultrasonic diagnosis apparatus at least partly mounted on the receptacle is slid and moved on the receptacle, and guides the ultrasonic diagnosis apparatus to the predetermined position on the receptacle while being in contact with at least part of the ultrasonic diagnosis apparatus.

12. The docking cart according to claim 10, wherein the first and second recessed portions are formed in the receptacle so as to prevent a hand of a person who grasps and mounts the ultrasonic diagnosis apparatus from coming into contact with the receptacle when at least part of the ultrasonic diagnosis apparatus is mounted on the receptacle.

13. The docking cart according to claim 11, wherein the first and second recessed portions are formed in the receptacle so as to prevent a hand of a person who grasps and mounts the ultrasonic diagnosis apparatus from coming into contact with the receptacle when at least part of the ultrasonic diagnosis apparatus is mounted on the receptacle.

14. The docking cart according to claim 10, wherein the receptacle is formed in such a manner that a front side of the docking cart becomes lower in level than a rear side of the docking cart.

15. The docking cart according to claim 10, wherein the sliding direction is a direction which goes to a rear side of the receptacle from a front side of the receptacle.

16. The docking cart according to claim 10, wherein the two foot portions are located on a rear side of the bottom surface in the ultrasonic diagnosis apparatus.

17. The docking cart according to claim 16, wherein the ultrasonic diagnosis apparatus includes two front foot portions other than the two foot portions, the two front foot portions being located on a front side of the bottom surface in the ultrasonic diagnosis apparatus.

18. The docking cart according to claim 17, further comprising a fitting portion including recessed shapes corresponding to shapes of the two front foot portions and that fix the ultrasonic diagnosis apparatus by fitting on the two front foot portions.

* * * * *